(12) United States Patent
Duclos et al.

(10) Patent No.: US 9,145,355 B2
(45) Date of Patent: Sep. 29, 2015

(54) PHENICOL ANTIBACTERIALS

(71) Applicant: Zoetis Services LLC, Florham Park, NJ (US)

(72) Inventors: Brian A. Duclos, Kalamazoo, MI (US); Richard Andrew Ewin, Kalamazoo, MI (US); Paul D. Johnson, Kalamazoo, MI (US); Timothy Allan Johnson, Kalamazoo, MI (US); Graham M. Kyne, Kalamazoo, MI (US); Derek James Sheehan, Kalamazoo, MI (US); Susan Mary Kult Sheehan, Kalamazoo, MI (US); Donald James Skalitzky, Ann Arbor, MI (US); Rajendran Vairagoundar, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/351,939

(22) PCT Filed: Oct. 5, 2012

(86) PCT No.: PCT/IB2012/055371
§ 371 (c)(1),
(2) Date: Apr. 15, 2014

(87) PCT Pub. No.: WO2013/057619
PCT Pub. Date: Apr. 25, 2013

(65) Prior Publication Data
US 2014/0303384 A1    Oct. 9, 2014

Related U.S. Application Data

(60) Provisional application No. 61/547,803, filed on Oct. 17, 2011.

(51) Int. Cl.
| | | |
|---|---|---|
| C07D 205/04 | (2006.01) |
| C07D 207/09 | (2006.01) |
| C07C 233/40 | (2006.01) |
| C07C 233/18 | (2006.01) |
| C07C 311/05 | (2006.01) |
| C07D 413/10 | (2006.01) |
| C07D 263/04 | (2006.01) |
| C07D 207/08 | (2006.01) |
| C07C 233/47 | (2006.01) |
| C07C 275/18 | (2006.01) |
| C07C 311/06 | (2006.01) |

(52) U.S. Cl.
CPC ............. *C07C 233/40* (2013.01); *C07C 233/18* (2013.01); *C07C 233/47* (2013.01); *C07C 275/18* (2013.01); *C07C 311/05* (2013.01); *C07C 311/06* (2013.01); *C07D 205/04* (2013.01); *C07D 207/08* (2013.01); *C07D 207/09* (2013.01); *C07D 263/04* (2013.01); *C07D 413/10* (2013.01); *C07C 2101/02* (2013.01)

(58) Field of Classification Search
None
See application file for complete search history.

(56) References Cited

FOREIGN PATENT DOCUMENTS

| WO | 03/077828 | 9/2003 |
| WO | 2012/125832 | 9/2012 |

OTHER PUBLICATIONS

PCT International Search Report, PCT/IB2012/055371, mailed Jan. 11, 2013 (4 pages).

*Primary Examiner* — Michael Barker
*Assistant Examiner* — Po-Chih Chen
(74) *Attorney, Agent, or Firm* — Martha A. Gammill

(57) ABSTRACT

The present invention provides novel phenicol derivatives, their use for the treatment of infections in mammals, pharmaceutical compositions containing these novel compounds, and methods for the preparation of these compounds.

2 Claims, No Drawings

PHENICOL ANTIBACTERIALS

FIELD OF THE INVENTION

The present invention provides novel phenicol derivatives, their use for the treatment of infections in mammals, pharmaceutical compositions containing these novel compounds, and methods for the preparation of these compounds.

BACKGROUND OF THE INVENTION

There is a growing need for new antibiotic agents for the treatment of bacterial infections in animals, and in particular there is a need for new agents which overcome increasing bacterial resistance to existing antibiotics.

Florfenicol is a broad spectrum phenicol antibiotic used exclusively in veterinary medicine. Phenicol antibiotics as a class are potent inhibitors of bacterial protein biosynthesis. Florfenicol has a broad spectrum of activity against many gram-negative and gram-positive bacteria, and is useful in the prevention and treatment of bacterial infections due to susceptible pathogens in birds, reptiles, fish, shellfish and mammals. An important use of florfenicol is in the treatment of respiratory infections in cattle, such as those caused by, for example, *Mannhemia haemolytica, Pasturella multocida* and *Haemophilus somnus*. Effective treatment of bovine respiratory disease (BRD) plays a significant role in reducing what is otherwise one of the leading causes of economic loss to both the dairy and beef industries worldwide.

Reports in recent years indicate that bacterial resistance to florfenicol is developing and has been observed across multiple bacterial genera and species, such as *Salmonella* (Bolton, L. F., et al., Clin. Microbiol. 1999, 37, 1348), *E. Coli* (Keyes, K., et al., Antimicrob. Agents Chemother., 2000, 44, 421), *Klebsiella pneumoniae* (Cloeckaert, A., et al., Antimicrob. Agents Chemother., 2001, 45, 2381), and in the aquacultural pathogen, *Photobacterium damselae* subsp. *piscicida* (formerly *Pasteurella piscicida*) (Kim, E., et al., Microbiol. Immunol., 1996, 40, 665). In light of the increasing threat of florfenicol resistance and the apparent mobility of the resistance genes across bacterial species and animal hosts (Cloeckaert, A., et al., Antimicrob. Agents Chemother., 2000, 44, 2858), there is an important need for new antibiotics that maintain or surpass the activity of florfenicol, while also overcoming the challenges of florfenicol resistance. The compounds of the present invention represent such an improvement.

SUMMARY OF THE INVENTION

The present invention provides a compound of formula I

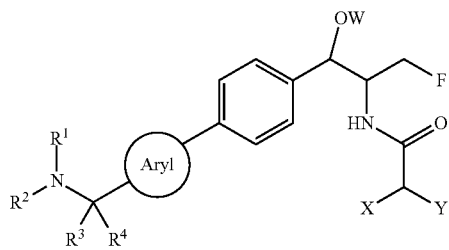

or pharmaceutical acceptable salts thereof wherein
Aryl moiety is phenyl or naphthyl, optionally substituted with one to three $R^6$;

$R^1$ is
a. H,
b. —$C_{1-8}$alkyl, optionally substituted with one or more OH, —SH, —CN, —NO$_2$, —NHR$^5$, —NC$_{1-4}$alkylR$^5$, —OC$_{1-4}$alkyl, —SC$_{1-4}$alkyl, —S(C=O)C$_{1-4}$alkyl, —C(=O)NR$^5$R$^5$, —SO$_2$NR$^5$, —SO$_2$R$^5$, or —C$_{3-6}$cycloalkyl,
c. —$C_{3-8}$cycloalkyl, optionally substituted with one to three $R^6$,
d. —SO$_2$R$^5$,
e. —C(=O)R$^5$, or
f. 4 to 6 membered heterocyclic ring moiety optionally contains one, two or three atoms selected from the group consisting from N, S and O, wherein the heterocyclic ring is optionally substituted with one to three $R^6$;

$R^2$ is
a. —$C_{1-8}$alkyl, optionally substituted with one or more OH, —SH, —CN, —NO$_2$, —NC$_{1-4}$alkylR$^5$, —OC$_{1-4}$alkyl, —SC$_{1-4}$alkyl, —S(C=O)C$_{1-4}$alkyl, —C(=O)NR$^5$R$^5$, —SO$_2$NR$^5$, —SO$_2$R$^5$, or —C$_{3-6}$cycloalkyl,
b. —$C_{3-8}$cycloalkyl, optionally substituted with one to three $R^6$,
c. —S(=O$_2$)R$^5$,
d. —C(=O)R$^5$, or
e. 4 to 6 membered heterocyclic ring moiety optionally contains one, two or three atoms selected from the group consisting from N, S and O, wherein the heterocyclic ring is optionally substituted with one to three $R^6$;

$R^3$ and $R^4$ are independently
a. —H,
b. —$C_{1-8}$alkyl optionally substituted with OH, —SH, halo, —CN, —NO$_2$, NH$_2$, —NHR$^5$, —NHR$^5$—OC$_{1-4}$alkyl, —SC$_{1-4}$alkyl, —S(C=O)C$_{1-4}$alkyl, —C(=O)NR$^5$R$^5$, —SO$_2$NR$^5$, or —SO$_2$R$^5$,
c. —$C_{3-8}$cycloalkyl, optionally substituted with one to three $R^6$,
d. —C(=O)C$_{1-8}$alkyl wherein alkyl is optionally substituted with —S(=O$_2$)R$^5$, —SO$_2$NR$^5$, or —C(=O)R$^5$,
e. 4 to 6 membered heterocyclic ring moiety optionally contains one, two or three atoms selected from the group consisting from N, S and O, wherein the heterocyclic ring is optionally substituted with one to three $R^6$,
f. $R^3$ and $R^4$ taken together form a $C_{3-8}$cycloalkyl, optionally substituted with one to three $R^6$; or
g. $R^3$ and $R^4$ taken together with one or two additional atoms selected from the group consisting from N, S and O form a 4 to 6 membered heterocyclic ring moiety, wherein the heterocyclic ring is optionally substituted with one to three $R^6$; or
$R^1$ and $R^2$, $R^1$ and $R^3$, or $R^2$ and $R^3$, taken together form a 4 to 6 membered heterocyclic ring moiety optionally contains one or two additional atoms selected from the group consisting from N, S and O, wherein the heterocyclic ring is optionally substituted with one to three $R^6$;
at each occurrence, $R^5$ is hydrogen, or $C_{1-6}$alkyl wherein said $C_{1-6}$alkyl is optionally substituted with one, two or three $R^6$;
at each occurrence, $R^6$ is OH, halo, —CN, —NO$_2$, —C$_{3-6}$cycloalkyl, —NH$_2$, —NHC$_{1-4}$alkyl, —N(C$_{1-4}$alkyl)$_2$, —OC$_{1-4}$alkyl, —SH, —SC$_{1-4}$alkyl, —S(C=O)C$_{1-4}$alkyl, —SONC$_{1-4}$alkyl, —C(=O)C$_{1-4}$alkyl, —C(=O)NH$_2$, —C(=O)NHC$_{1-4}$alkyl, —C(=O)N(C$_{1-4}$alkyl)$_2$, —NC(=O)NH$_2$, —NC(=O)NHC$_{1-4}$alkyl, or NC(=O)N(C$_{1-4}$alkyl)$_2$;
W is —H, —PO(OH)$_2$, —CH$_2$PO(OH)$_2$, —C(=O)C$_{1-4}$alkyl, or —CH$_2$OC(=O)C$_{1-4}$alkyl, wherein C$_{1-4}$alkyl is optionally substituted with —OCO$_2$H, —OCO$_2$C$_{1-4}$alkyl, or —OC(=O)NHC$_{1-4}$alkyl;

X and Y are independently halo, $C_{1-4}$alkyl, $CF_3$, $-NH_2$, $-CN$, or $N_3$; and with proviso that when one of $R_3$ and $R_4$ is $-C_{1-8}$alkyl; then $R_2$ may be H.

In another aspect, the present invention also provides:

pharmaceutical compositions which comprise a pharmaceutically acceptable carrier and a compound of formula I, methods for controlling or treating infections in mammals by administering to a mammal in need of a therapeutically effective amount of a compound of formula I or a pharmaceutically acceptable salt thereof, methods for controlling or treating infections in livestock caused and companion animal by administering to a mammal in need a therapeutically effective amount of a compound of formula I or a pharmaceutically acceptable salt thereof, methods for the preparation of compounds of the present invention, and use of the compounds of the present invention to prepare medicaments for controlling or treating infections in livestock in need thereof.

DETAILED DESCRIPTION

With respect to the above compound, and throughout the application and claims, the following terms have the meanings defined below.

The term "halo" refers to chloro, bromo, fluoro, and iodo.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-4}$ alkyl refers to alkyl of one to four carbon atoms, inclusive; $C_{1-6}$ alkyl refers to alkyl of one to six carbon atoms, inclusive; and $C_{1-8}$ alkyl refers to alkyl of one to eight carbon atoms, inclusive.

The term alkyl refers to straight, branched and a cyclic saturated monovalent hydrocarbon groups, but reference to an individual radical such as "propyl" embraces only the straight chain radical, a branched chain isomer such as "isopropyl" or a cyclic isomer such as cyclopropylmethyl or cyclopentyl being specifically referred to.

The term "cycloalkyl" refers to a mono ring such as cyclopropyl, cyclobutyl, cyclopentyl, or cyclohexyl.

The term "aryl" refers to a cyclic or polycyclic aromatic ring having from 5 to 12 carbon atoms.

The term "heterocyclic" refers to a saturated or unsaturated mono-cyclic group containing at least one heteroatom selected from N, O, and S. Examples of heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxcithiazinyl, indolinyl, isoindolinyl, quincuclidinyl, chromanyl, isochromanyl, benzocazinyl, and the like. Examples of monocyclic saturated or unsaturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl.

The term "mammal" refers to human or animals including livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys. Specifically, livestock animals of the present invention refer to cattle and pigs.

The term "controlling", "treating" or "treatment" of a disease includes: (1) preventing the disease, i.e. causing the clinical symptoms or signs of the disease not to develop in a mammal that may be exposed to or predisposed to the disease but does not yet experience or display symptoms/signs of the disease; (2) inhibiting the disease, i.e., arresting or reducing the development of the disease or its clinical symptoms/signs; or (3) relieving the disease, i.e., causing regression of the disease or its clinical symptoms/signs.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "pharmaceutically acceptable" means suitable for use in mammals, companion animals or livestock animals.

The term "prodrug" refers to a bio-reversible derivative of a molecule, i.e. a compound of formula I of the present invention. Prodrugs can alter the solubility, lipophilicity and in-vivo distribution of drugs. By deliberately altering these key properties, it may be possible to improve absorption, enhance onset time, reduce first pass metabolism, allow development of aqueous IV formulations and achieve targeted delivery. In addition, prodrugs are useful in improving transdermal delivery, masking taste, minimizing pain on injection, improving stability, etc. In situations where the pharmacophore itself leads to poor delivery properties, prodrugs are one of the few strategies that can be used to salvage the highly active compound. Included within the scope of the present invention are all prodrugs of the compounds of formula I that can be prepared by the standard methods known to one skilled in the art. Prodrugs of the compounds of formula I may be prepared following the methods described in "Prodrugs of phosphates, phosphonates, and phosphinates", Krise J P, Stella V J, Advanced Drug Delivery Reviews, 19: (2) 287-310 May 22, 1996; "Targeted Prodrug Design to Optimize Drug Delivery". Hyo-Kyung Han and Gordon Amidon. AAPS Pharm Sci 2000; 2 (1) article 6; "Prodrugs", L. Prokai and K. Prokai-Tatrai, Chapter 12 in *Injectable Drug Development: Techniques to Reduce Pain and Irritation*, Interpharm Press, Buffalo Grove, Ind., 1999; "Improved oral drug delivery: Solubility limitations overcome by the use of prodrugs", Fleisher D, Bong R, Stewart B H, Advanced Drug Delivery Reviews, 19: (2) 115-130 May 22, 1996; or "Preparation and hydrolysis of water soluble, non-irritating prodrugs of pharmaceuticals with oxaalkanoic acids", Crooks, Peter Anthony; Cynkowski, Tadeusz; Cynkowska, Grazyna; Guo, Hong; Ashton, Paul. PCT Int. Appl. (2000), 65 pp.

Compounds that have the same molecular formula but differ in the nature or sequence of bonding of their atoms or the arrangement of their atoms in space are termed "isomers".

Included within the scope of the described compounds are all isomers (e.g. cis-, trans-, enantiomers, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds.

Specifically, the present invention provides a compound of formula IA

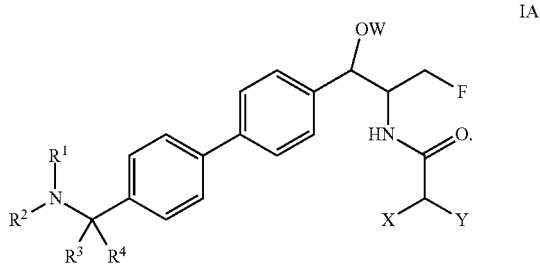

Specifically, the present invention provides a compound of formula IB

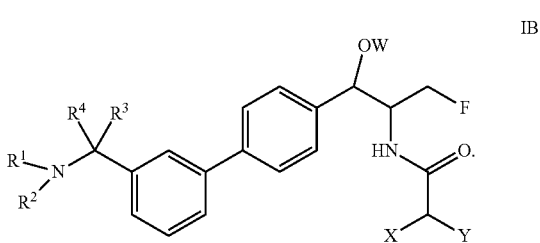

Specifically, the compounds of the present invention are compounds of formula I wherein $R^2$ is $C_{1-8}$alkyl.

Specifically, a compound of formula I wherein $R^2$ is alkyl substituted with —$C_{3-6}$cycloalkyl, —$NHC_{1-4}$alkyl, or —$N(C_{1-4}$alkyl$)_2$.

Specifically $R^2$ is —$SO_2C_{1-4}$alkyl.

Specifically, a compound of formula I wherein $R^3$ and $R^4$ are independently H.

Specifically, a compound of formula I wherein $R^3$ and $R^4$ taken together form a $C_{3-8}$cycloalkyl.

Specifically, a compound of formula I wherein $R^3$ and $R^4$ taken together with one or two additional atoms selected from the group consisting from N, S and O form a 4 to 6 membered heterocyclic ring moiety.

Specifically, a compound of formula I wherein $R^3$ and $R^4$ taken together with an oxygen atom form a 4 to 6 membered heterocyclic ring moiety.

Specifically, a compound of formula I wherein $R^3$ and $R^4$ taken together form a 4 to 6 membered heterocyclic ring moiety which optionally contains a group selected from group consisting of —S—, —S(=O)—, —S(=O$_2$)—, —NH—, and —NR$^5$—.

Specifically, a compound of formula I wherein $R^1$ and $R^2$ taken together form a 4 to 6 membered heterocyclic ring moiety optionally contains one or two additional atoms selected from the group consisting from N, S and O.

Specifically, a compound of formula I wherein $R^1$ and $R^2$ taken together form a 4 to 6 membered heterocyclic ring moiety optionally contains one or two additional atoms selected from the group consisting from N, S and O.

Specifically, a compound of formula I wherein $R^1$ and $R^2$ taken together form a 4 to 6 membered heterocyclic ring moiety which further contains a group selected from group consisting of —S—, —S(=O)—, —S(=O$_2$)—, —NH—, and —NR$^5$—.

Specifically, a compound of formula I wherein $R^2$ and $R^3$ taken together with the nitrogen to which they attach form a 4 to 6 membered heterocyclic ring moiety.

Specifically, at each occurrence, heterocyclic ring moiety is optionally substituted with $R^6$.

Specifically, $R^5$ is hydrogen, or $C_{1-6}$alkyl.

Specifically, $R^6$ is hydrogen, OH, halo, —CN, —NO$_2$, NH$_2$, —NHC$_{1-4}$alkyl, —N(C$_{1-4}$alkyl)$_2$, —OC$_{1-3}$alkyl, —NHC(=O)OC$_{1-4}$alkyl, or C$_{1-6}$alkyl wherein said C$_{1-6}$alkyl is optionally substituted with OH, halo, C$_{3-6}$cycloalkyl, —NH$_2$, —NHC$_{1-4}$alkyl, —N(C$_{1-4}$alkyl)$_2$, —OC$_{1-4}$alkyl, —SH, —SC$_{1-4}$alkyl, —S(C=O)C$_{1-4}$alkyl, —C(=O)C$_{1-4}$alkyl, S(=O$_2$)C$_{1-8}$alkyl, —SO$_2$NR$^5$, —C(=O)NH$_2$, —C(=O)NHC$_{1-4}$alkyl, —C(=O)N(C$_{1-4}$alkyl)$_2$, —NHC(=O)NH$_2$, —NHC(=O)OC$_{1-4}$ alkyl, or NHC(=O)N(C$_{1-4}$alkyl)$_2$.

Examples of the present invention include:
a) 2,2-Dichloro-N-((1R,2S)-3-fluoro-1-hydroxy-1(4'-(methylsulfonamidomethyl)-[1,1'-biphenyl]-4-yl)propan-2-yl) acetamide,
b) 2,2-Dichloro-N-((1R,2S)-3-fluoro-1-hydroxy-1-(4'-((3-methylureido)methyl)-[1,1-biphenyl]-4-yl)propan-2-yl) acetamide,
c) N-((1R,2S)-1-(4'-(Acetamidomethyl)-[1,1'-biphenyl]-4-yl)-3-fluoro-1-hydroxypropan-2-yl)-2,2-dichloroacetamide,
d) N-((1R,2S)-1-(4'-(2-aminopropan-2-yl)-[1,1'-biphenyl]-4-yl)-3-fluoro-1-hydroxypropan-2-yl)-2,2-dichloroacetamide,
e) N-((1R,2S)-1-(4'-((R)-1-aminoethyl)-[1,1'-biphenyl]-4-yl)-3-fluoro-1-hydroxypropan-2-yl)-2,2-dichloroacetamide,
f) 2,2-dichloro-N-((1R,2S)-3-fluoro-1-hydroxy-1-(4'-(pyrrolidin-2-yl)-[1,1-biphenyl]-4-yl)propan-2-yl)acetamide,
g) N-((1R,2S)-1-(4'-(azetidin-2-yl)-[1,1'-biphenyl]-4-yl)-3-fluoro-1-hydroxypropan-2-yl)-2,2-dichloroacetamide,
h) 2,2-dichloro-N-((1R,2S)-3-fluoro-1-(4'-((3-fluoroazetidin-1-yl)methyl)-[1,1'-biphenyl]-4-yl)-1-hydroxypropan-2-yl)acetamide,
i) 2,2-dichloro-N-((1R,2S)-3-fluoro-1-(4'-((3-fluoroazetidin-1-yl)methyl)-[1,1'-biphenyl]-4-yl)-1-hydroxypropan-2-yl)acetamide,
j) 2,2-dichloro-N-((1R,2S)-3-fluoro-1-hydroxy-1-(4'-((3-((methylamino)methyl)azetidin-1-yl)methyl)-[1,1-biphenyl]-4-yl)propan-2-yl)acetamide,
k) 2,2-dichloro-N-((1R,2S)-3-fluoro-1-hydroxy-1-(4'-((3-hydroxyazetidin-1-yl)methyl)-[1,1-biphenyl]-4-yl)propan-2-yl)acetamide,
l) 2,2-dichloro-N-((1R,2S)-1-(4'-((3-(dimethylamino)azetidin-1-yl)methyl)-[1,1-biphenyl]-4-yl)-3-fluoro-1-hydroxypropan-2-yl)acetamide,
m) N-((1R,2S)-1-(4'-((3-(aminomethyl)azetidin-1-yl)methyl)-[1,1'-biphenyl]-4-yl)-3-fluoro-1-hydroxypropan-2-yl)-2,2-dichloroacetamide,
n) 2,2-dichloro-N-((1R,2S)-3-fluoro-1-hydroxy-1-(4'-((3-methoxyazetidin-1-yl)methyl)-[1,1'-biphenyl]-4-yl)propan-2-yl)acetamide,
o) N-((1R,2S)-1-(4'-((3-acetamidoazetidin-1-yl)methyl)-[1,1'-biphenyl]-4-yl)-3-fluoro-1-hydroxypropan-2-yl)-2,2-dichloroacetamide,
p) N-((1R,2S)-1-(4'-((3-aminoazetidin-1-yl)methyl)-[1,1'-biphenyl]-4-yl)-3-fluoro-1-hydroxypropan-2-yl)-2,2-dichloroacetamide,
q) 2,2-dichloro-N-((1R,2S)-3-fluoro-1-hydroxy-1-(4'-((3-hydroxy-3-(trifluoromethyl)azetidin-1-yl)methyl)-[1,1'-biphenyl]-4-yl)propan-2-yl)acetamide,
r) 2,2-dichloro-N-((1R,2S)-3-fluoro-1-hydroxy-1-(4'-((3-(trifluoromethyl)azetidin-1-yl)methyl)-[1,1-biphenyl]-4-yl)propan-2-yl)acetamide, or
s) N-((1R,2S)-1-(4'-((3-(aminomethyl)-3-hydroxyazetidin-1-yl)methyl)-[1,1'-biphenyl]-4-yl)-3-fluoro-1-hydroxypropan-2-yl)-2,2-dichloroacetamide.

The following reaction schemes illustrate the general synthetic procedures of the compounds of the present invention.

All starting materials are prepared by procedures described in these schemes or by procedures known to one of ordinary skill in the art.

Scheme I

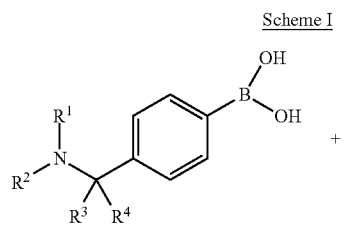

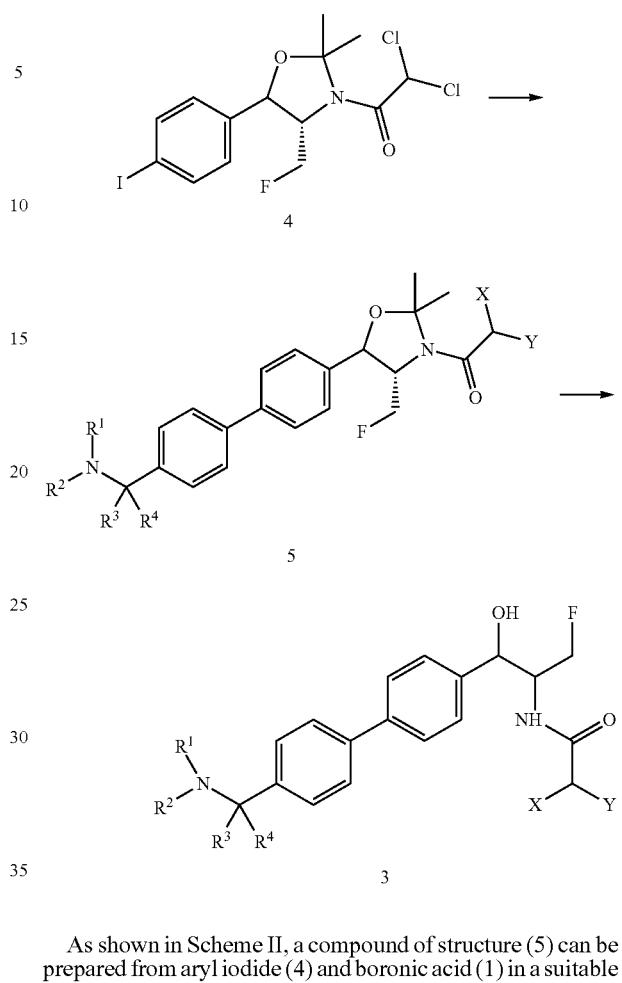

As shown in Scheme I, a compound of structure (2) can be prepared from commercially available (1R,2S)-2-amino-3-fluoro-1-(4-iodophenyl)propan-1-ol in the presence of an ethyldihaloacetate and a suitable base such as triethylamine in a suitable polar protic solvent such methanol or isopropyl alcohol at temperatures from room temperature to reflux. A compound of structure (3) can be prepared from a boronic acid (1) and aryl iodide (2) in a suitable solvent such as 1,4-dioxane or tetrahydrofuran or water, in the presence of a suitable catalyst such as palladium tetrakis triphenylphosphine and a suitable base such as cesium carbonate or potassium carbonate at temperature between room temperature and 100° C. In the reaction $R^1$, $R^2$, $R^3$ and $R^4$ are previously defined, X and Y are halogen.

Scheme II

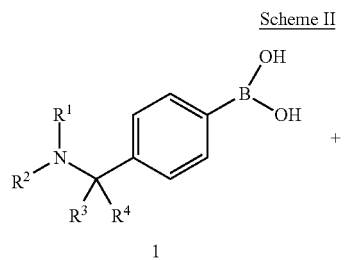

As shown in Scheme II, a compound of structure (5) can be prepared from aryl iodide (4) and boronic acid (1) in a suitable solvent such as 1,4-dioaxane or tetrahydrofuran or water, in the presence of a suitable catalyst such as palladium tetrakis triphenylphosphine and a suitable base such as cesium carbonate or potassium carbonate at temperature between room temperature and 100° C. In the reaction $R^1$, $R^2$, $R^3$ and $R^4$ are previously defined, X and Y are halogen. A compound of structure (3) can be prepared from a compound (5) in the presence of an organic acid such as 1,1,1-trifluoroacetic acid or inorganic acid such as hydrochloric or sulfuric acid in a suitable solvent such as dichloromethane or 1,4-dioxane or water at temperature between 0° C. and reflux.

Scheme III

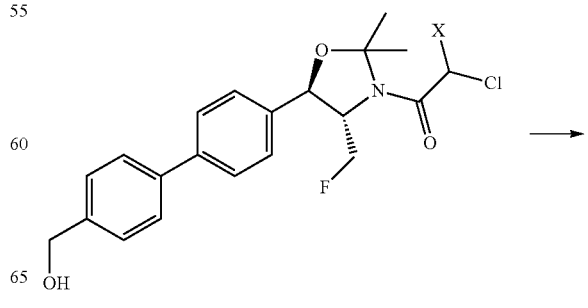

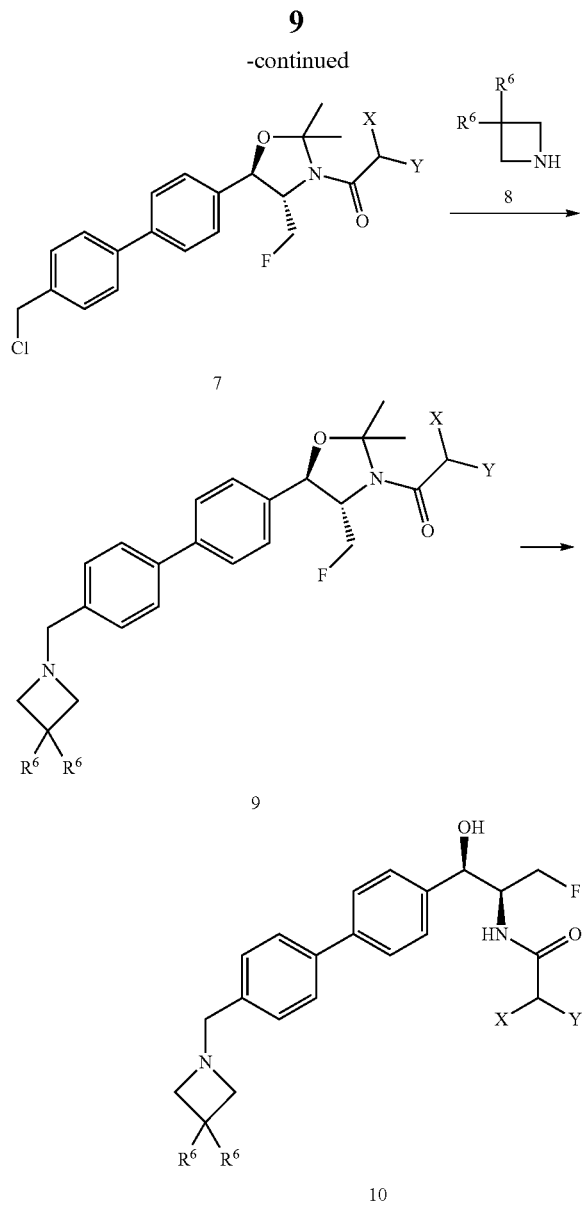

As shown in Scheme III, a compound of structure (6) can be prepared according to the method described in preparation 7 in the Examples in a suitable solvent such as 1,4-dioxane or tetrahydrofuran or water, in the presence of a suitable catalyst such as palladium tetrakis triphenylphosphine and a suitable base such as cesium carbonate or potassium carbonate at temperature between room temperature and 100° C. A compound of structure (7) can be prepared from a compound of structure (6) using a suitable chlorinating agent such as thionyl chloride or methane sulfonyl chloride in the presence of a suitable base such as triethylamine or diisopropylethylamine in a suitable solvent such as dichlromethane or tetrahydrofuran at temperatures between 0° C. and reflux. A compound of structure (9) can be prepared in the presence of commercially available azetidines (8) in the presence of a suitable base such as triethylamine or diisopropylethylamine in a polar aprotic solvent such as dimethylformamide or NMP at temperature from room temperature to 100° C. A compound of structure 10 can be prepared from a compound of structure (9) in the presence of an organic acid such as 1,1,1-trifluoroacetic acid or inorganic acid such as hydrochloric or sulfuric acid in a suitable solvent such as dichloromethane or 1,4-dioxane or water at temperature between 0° C. and reflux.

Pharmaceutical Salts

The compound of formula I may be used in its native form or as a salt. In cases where forming a stable nontoxic acid or base salt is desired, administration of the compound as a pharmaceutically acceptable salt may be appropriate. Pharmaceutically acceptable salts of the compounds of formula I include the acetate, ascorbate, aspartate, benzoate, besylate, bicarbonatecarbonate, bisulphatesulphate, borate, camsylate, citrate, edisylate, etoglutarate, esylate, formate, fumarate, gluceptate, gluconate, glucuronate, glycerophosphate, hexafluorophosphate, hibenzate, hydrochloridechloride, hydrobromidebromide, hydroiodideiodide, isethionate, lactate, malate, maleate, malonate, mesylate, methylsulphate, naphthylate, 2-napsylate, nicotinate, nitrate, orotate, oxalate, palmitate, pamoate, phosphatehydrogen phosphatedihydrogen phosphate, saccharate, stearate, succinate, tartrate, tosylate and trifluoroacetate salts.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, extended-releasing, or controlled-releasing. Specifically, the formulation of the invention can be an extended release form. Thus, the pharmaceutical formulations can also be formulated for controlled release or for slow release.

Dosage

Pharmaceutical compositions suitable for use in the present invention include compositions wherein the active ingredients are contained in an amount sufficient to achieve the intended purpose, i.e., control or the treatment of infections. More specifically, a therapeutically effective amount means an amount of compound effective to prevent, alleviate or ameliorate symptoms/signs of infections or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.1 mg to about 20 mg/kg of body weight/day, preferably about 0.1 to about 5 mg/kg of body weight/day. It is to be understood that the dosages may vary depending upon the requirements of each subject and the severity of the infections.

The desired dose may conveniently be presented in a single dose or as divided doses administered at appropriate intervals, for example, as two, three, four or more sub-doses per day. Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

Compounds of the present invention provides novel phenicol antibacterial agents for the treatment of bovine respiratory disease infections in cattle caused by Gram-negative respiratory pathogens such as *M. haemolytica, P. multocida, H. somnus,* and *M. bovis.*

Antibacterial Assays

Compounds of the present invention are tested against an assortment of Gram-negative and Gram-positive organisms using the industrial standard techniques described in *Methods for Dilution Antimicrobial Susceptibility Tests for Bacteria That grow Aerobically; Approved Standard—Eighth Edition,* M07-A8, Vol. 29 No. 2 Replaces M07-A7 Vol. 26 No. 2. The compounds of the present invention demonstrate very good antibacterial activity against BRD pathogens *M. haemolytica* and *P. multo.*

EXAMPLES

The synthesis of compounds of the present invention is further illustrated by the following examples. The starting materials and various intermediates utilized in the examples may be obtained from commercial sources, or are readily prepared from commercially available organic compounds, using well-known methods to one skilled in the art.

Preparation 1: 2,2-Dichloro-N-((1R,2S)-3-fluoro-1-hydroxy-1-(4-iodophenyl)propan-2-yl)acetamide

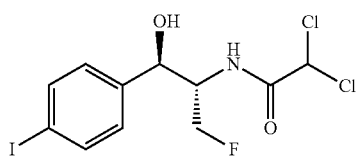 [SMILES: O=C(N[C@H](CF)[C@H](O)c1ccc(I)cc1)C(Cl)Cl]

To a solution of commercially available (1R,2S)-2-amino-3-fluoro-1-(4-iodophenyl)propan-1-ol (5.0 g, 20.0 mmol) in methanol (100 mL) is added triethylamine (9.56 mL, 67.8 mmol) and ethyldichloroacetate (6.22 mL, 50.8 mmol) and the mixture heated to reflux for 16 hours. After allowing to cool to room temperature, the solvent is removed under reduced pressure the resultant oil purified by column chromatography eluting from neat heptanes to 80% ethylacetate/heptanes to give the title compound (5.94 g). m/z (Cl) M+H 405.

Preparation 2: 2,2-Dichloro-N-((1R,2S)-3-fluoro-1-hydroxy-1-(4-(trimethylstannyl)phenyl)-propan-2-yl)acetamide

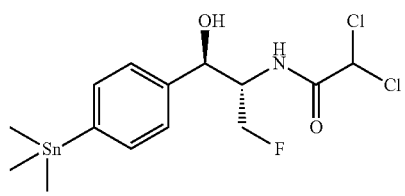 [SMILES: [CH3][Sn]([CH3])([CH3])[c]1ccc([C@@H](O)[C@@H](CF)NC(=O)C(Cl)Cl)cc1]

Hexamethylditin (196 mg, 0.59 mmol) is added to a degassed solution of the product of preparation 1 (0.20 g, 1.00 mmol) palladiumtetrakistriphenyl-phosphine (30 mg, 0.025 mmol) in toluene (10 ml), the mixture is heated to reflux for 3 hours. The mixture is cooled and filtered through a plug of celite. The filtrates are partitioned between DCM and water. The organics are separated, dried over MgSO₄, filtered and evaporated to give a residue, which is purified using column chromatography eluting from neat heptanes to neat EtOAc to give the title compound (37 mg): m/z (Cl) M+H 443.

Preparation 3: Tert-butyl ((4'-((1R,2S)-2-(2,2-dichloroacetamido)-3-fluoro-1-hydroxypropyl)-[1,1'-biphenyl]-4-yl)methyl)carbamate

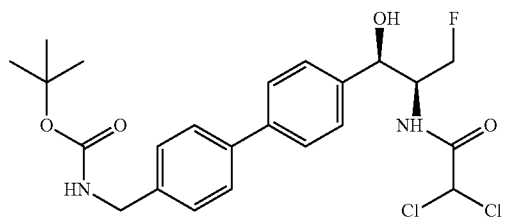 [SMILES: CC(C)(C)OC(=O)NCc1ccc(-c2ccc([C@@H](O)[C@@H](CF)NC(=O)C(Cl)Cl)cc2)cc1]

To solution of commercially available (4-(((tert-butoxycarbonyl)-amino)methyl)-phenyl)boronic acid (1.01 gm, 4.02 mmol) in 1,4-dioxane:water (12.3:3.8 mL) is added 2,2-dichloro-N-((1R,2S)-3-fluoro-1-hydroxy-1-(4-iodophenyl) propan-2-yl)acetamide (1.04 g, 2.56 mmol) and CS₂CO₃ (1.85 g, 5.67 mmol) and the resulting solution bubbled with nitrogen gas for 30 min. To this reaction mixture is added Pd(PPh₃)₄ (0.332 g, 0.29 mmol) and the resulting reaction mixture heated to 110° C. for 2 hours. The resulting reaction mixture is cooled, diluted with water and extracted with ethyl acetate. The organic layer dried over sodium sulfate and concentrated to give a crude residue, which is purified using column chromatography on silica gel eluting with 30% Ethyl acetate/hexane to give the title compound (668 mg). 1H NMR (400 MHz, CDCl3) δ: 1.46 (s, 8H), 4.30-4.32 (m, 1H), 4.34-4.35 (m, 2H), 4.44-4.47 (m, 0.5H), 4.55-4.59 (m, 1H), 4.68-4.69 (m, 0.5H), 4.85 (m, 1H), 5.15 (t, 1H, J=7.04 Hz), 5.87 (s, 1H), 7.04 (d, 1H, J=8.6 Hz), 7.34 (d, 2H, J=7.92 Hz), 7.44 (d, 2H, J=8.2 Hz), 7.53 (d, 2H, J=8.08 Hz), 7.57 (d, 2H, J=8.08 Hz). m/z (Cl) M−H 483

Preparation 4: N-((1R,2S)-1-(4'-(Aminomethyl)-[1,1'-biphenyl]-4-yl)-3-fluoro-1-hydroxypropan-2-yl)-2,2-dichloroacetamide

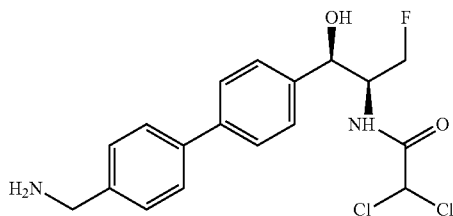 [SMILES: NCc1ccc(-c2ccc([C@@H](O)[C@@H](CF)NC(=O)C(Cl)Cl)cc2)cc1]

To a solution of the product of preparation 3 (660 mg, 1.36 mmol) in DCM (2 mL), is added TFA (2 mL) at 0° C. and stirring continued for 2 hours. The reaction mixture is concentrated and the residue diluted with water. The solution is made basic with aqueous ammonia and extracted with chloroform. The organic layer is dried over sodium sulfate and concentrated to give the title compound (436 mg). 1H NMR (400 MHz, DMSO-$d_6$) δ 3.73 (s, 2H), 4.17-4.21 (m, 1H), 4.28-4.30 (m, 0.5H), 4.38-4.42 (m, 0.5H), 4.55-4.58 (m, 0.5H), 4.66-4.70 (m, 0.5H), 4.87 (t, 1H J=7.08 Hz), 5.96-5.97 (d, 1H, J=4.12 Hz), 6.53 (s, 1H), 7.40 (t, 3H), 7.57-7.60 (m, 4H), 8.64 (d, 1H, J=8.76 Hz). m/z (Cl) M+H 385.

Preparation 5: (4S,5R)-4-(Fluoromethyl)-5-(4-iodophenyl)-2,2-dimethyloxazolidine

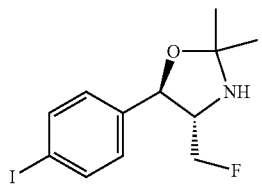 [SMILES: CC1(C)N[C@H](CF)[C@@H](c2ccc(I)cc2)O1]

Commercially available (1R,2S)-2-amino-3-fluoro-1-(4-iodophenyl)propan-1-ol (6.0 g, 20.0 mmol) is dissolved in acetone (150 mL) and the mixture stirred at room temperature for 16 hours. The solvent is removed under reduced pressure to give the title compound (7.0 g). m/z (Cl) M+H 295.

Preparation 6: Tert-butyl 2-(4-bromophenyl)azetidine-1-carboxylate

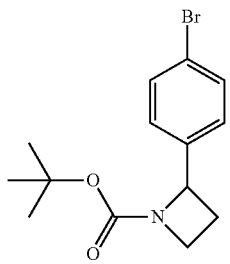 [SMILES: CC(C)(C)OC(=O)N1CCC1c1ccc(Br)cc1]

To a stirred solution of 2-(4-bromophenyl)azetidine (0.200 g, 2.19 mmol) in 1,4-dioxane (4 mL) is added BOC anhydride (0.193 g, 0.89 mmol). Potassium carbonate (0.134 g, 0.96 mmol) in water (1 mL) is added and allowed to stir to room temperature for 16 hours. The reaction mixture is concentrated in vacuo, and the resultant residue diluted with water and extracted with DCM. Organic layer is separated and concentrated to give the title compound (230 mg): m/z (Cl) M+H 311.

Preparation 7: 2,2-dichloro-1-((4S,5R)-4-(fluoromethyl)-5-(4'-(hydroxymethyl)-[1,1'-biphenyl]-4-yl)-2,2-dimethyloxazolidin-3-yl)ethanone

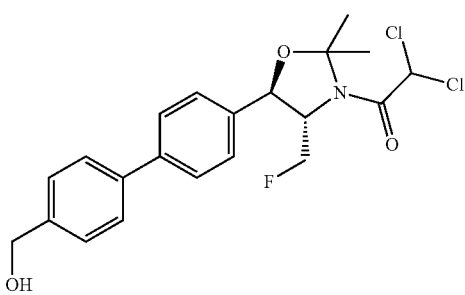 [SMILES: CC1(C)O[C@H](c2ccc(-c3ccc(CO)cc3)cc2)[C@@H](CF)N1C(=O)C(Cl)Cl]

A mixture of (4-(hydroxymethyl)phenyl)boronic acid (2.5 g, 16.8 mmol), 2,2-dichloro-1-((4S,5R)-4-(fluoromethyl)-5-(4-iodophenyl)-2,2-dimethyloxazolidin-3-yl)ethanone (5.0 g, 11.21 mmol) $Cs_2CO_3$ (7.3 g, 22.4 mmol) and $Pd(PPh_3)_4$ (1.3 g, 1.12 mmol) dioxane (100 mL) and water (30 mL) is heated at 80° C. for 4 hours under nitrogen. Reaction is cooled, washed with water (30 mL), dried over $Na_2SO_4$, and concentrated to a syrup. Crude compound adsorbed on celite and purified on silica gel column eluting from 10% to 50% EtOAC/heptane to get the title compound (3.2 g): 1H NMR (400 MHz, CDCl$_3$) δ: (1H NMR) 1.68 (bs, 3H), 1.75 (bs, 3H), 4.50-4.75 (m, 2H), 4.78 (d, 2H, J=6.0 Hz) 4.80-4.87 (m, 0.5H) 5.0-5.13 (br, 1H), 5.14-5.3 (m, 0.5H), 6.2-6.41 (br, 1H), 7.48 (d, 1H, J=8 Hz), 7.53 (d, 1H, J=8.0 Hz), 7.62 (d, 1H, J=8.0 Hz), 7.65 (d, 1H, J=8.0 Hz), (m/z (Cl) 368 [M-($CH_3$)$_2$CO].

Preparation 8: 2,2-dichloro-1-((4S,5R)-5-(4'-(chloromethyl)-[1,1'-biphenyl]-4-yl)-4-(fluoromethyl)-2,2-dimethyloxazolidin-3-yl)ethanone

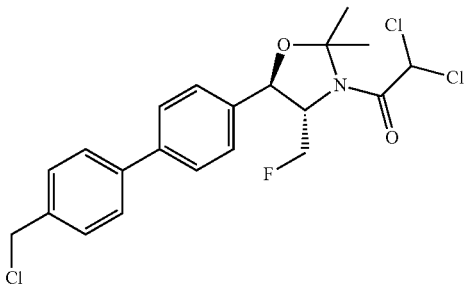 [SMILES: CC1(C)O[C@H](c2ccc(-c3ccc(CCl)cc3)cc2)[C@@H](CF)N1C(=O)C(Cl)Cl]

To an ice-water cooled solution of the product of preparation 7 (3.0 g, 7.0 mmol) in DCM (50 mL) is added diisopropylethylamine (4.3 mL, 24.6 mmol) and methane sulfonyl chloride (1.37 mL, 17.6 mmol) and then resulting mixture is stirred at room temperature for 9 hours. Reaction is washed with water (3×25 mL), dried over $Na_2SO_4$ and concentrated to a syrup. Crude product adsorbed on celite and purified on silica gel column eluting from 0 to 30% EtOAC/heptane (10 CV) to get the title compound (3.0 g): 1H NMR (400 MHz, DMSO-$d_6$) δ: (1H-NMR) 1.50 (s, 3H), 1.62 (s, 3H), 4.48-4.57

(m, 0.5H), 4.60-4.68 (m, 0.5H), 4.69-4.76 (m, 0.5H) 4.78-4.87 (m, 2.5H), 4.88-4.98 (m, 1H), 5.2-5.26 (m, 1H), 7.04 (s, 1H), 7.49-7.62 (m, 4H), 7.67-7.78 (m, 4H), (m/z (Cl) 388 [M-(CH$_3$)$_2$CO].

Example 1

2,2-Dichloro-N-((1R,2S)-3-fluoro-1-hydroxy-1-(4'-(methylsulfonamidomethyl)-[1,1-biphenyl]-4-yl)propan-2-yl)acetamide

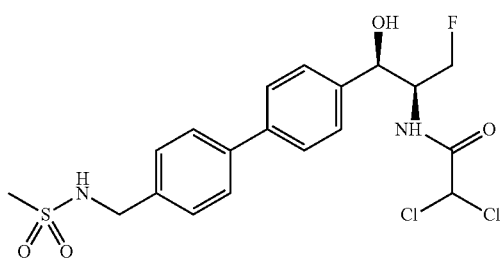 [SMILES: CS(=O)(=O)NCc1ccc(-c2ccc([C@@H](O)[C@@H](CF)NC(=O)C(Cl)Cl)cc2)cc1]

To a solution of the product of preparation 4 (35 mg, 0.091 mmol) in pyridine (0.5 mL) is added DMAP (0.1 mg, 0.0091 mmol) and the mixture cooled to 0° C. Methanesulfonyl chloride (7.9 μL, 0.1 mmol) is added dropwise and the mixture allowed to warm to room temperature, the reaction mixture is stirred for 3 hours. The solvent is then removed under reduced pressure and the residue purified by HPLC to afford the title compound (23.6 mg). $^1$H NMR (400 MHz, CDCl$_3$): δ 8.62 (d, J=8 Hz, 1H), 7.57-7.66 (m, 9H), 6.54 (s, 1H), 5.96 (m, 1H), 4.89 (m, 1H), 4.62 (dm, J=48 Hz, 1H), 4.36 (dm, J=48 Hz, 1H), 4.20 (d, J=8 Hz, 2H), 2.88 (s, 3H).

Example 2

2,2-Dichloro-N-((1R,2S)-3-fluoro-1-hydroxy-1-(4'-((3-methylureido)methyl)-[1,1'-biphenyl]-4-yl)propan-2-yl)acetamide

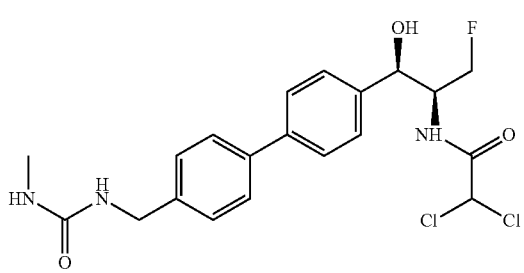 [SMILES: CNC(=O)NCc1ccc(-c2ccc([C@@H](O)[C@@H](CF)NC(=O)C(Cl)Cl)cc2)cc1]

To a solution of the product of preparation 4 (35 mg, 0.091 mmol) in dichloromethane (0.61 mL) and triethylamine (28.1 μL, 0.2 mmol) at 0° C. is added methylisocyanate (5.9 μL, 0.1 mmol). The combined mixture is stirred at 0° C. for 15 min, concentrated in vacuo, and purified by HPLC to afford the title compound (33.8 mg). $^1$H NMR (400 MHz, CDCl$_3$): δ 8.62 (d, J=8 Hz, 1H), 7.60 (m, 4H), 7.41 (d, J=8 Hz, 2H), 7.32 (d, J=8 Hz, 2H), 6.54 (s, 1H), 6.40 (m, 1H), 5.96 (m, 1H), 5.82 (m, 1H), 4.89 (m, 1H), 4.63 (dm, J=56 Hz, 1H), 4.34 (dm, J=56 Hz, 1H), 4.22 (d, J=8 Hz, 2H), 2.57 (d, J=12 Hz, 3H).

Example 3

N-((1R,2S)-1-(4'-(Acetamidomethyl)-[1,1-biphenyl]-4-yl)-3-fluoro-1-hydroxypropan-2-yl)-2,2-dichloroacetamide

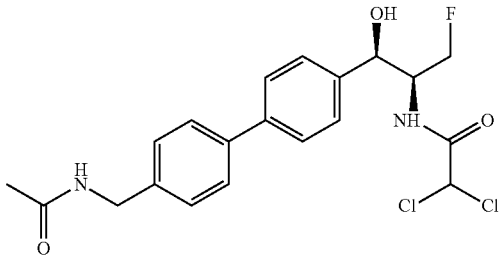 [SMILES: CC(=O)NCc1ccc(-c2ccc([C@@H](O)[C@@H](CF)NC(=O)C(Cl)Cl)cc2)cc1]

To a solution of the product of preparation 4 (35 mg, 0.091 mmol) in pyridine (0.5 mL) is added DMAP (0.1 mg, 0.0091 mmol) and the combined mixture cooled to 0° C. Acetic anhydride (10 μL, 0.1 mmol) is then added dropwise and the mixture allowed to warm to ambient temperature and stir for 3 hours. Solvents are then removed in vacuo and the residue purified by HPLC to afford the title compound (23.2 mg). $^1$H NMR (400 MHz, CDCl$_3$): δ 8.62 (d, J=8 Hz, 1H), 8.37 (m, 1H), 7.60 (m, 4H), 7.41 (d, J=8 Hz, 2H), 7.33 (d, J=8 Hz, 2H), 6.54 (s, 1H), 4.88 (m, 1H), 4.63 (dm, J=52 Hz, 1H), 4.34 (dm, J=52 Hz, 1H), 4.28 (d, J=8 Hz, 2H), 1.88 (s, 1H).

Example 4

N-((1R,2S)-1-(4'-(2-aminopropan-2-yl)-[1,1-biphenyl]-4-yl)-3-fluoro-1-hydroxypropan-2-yl)-2,2-dichloroacetamide

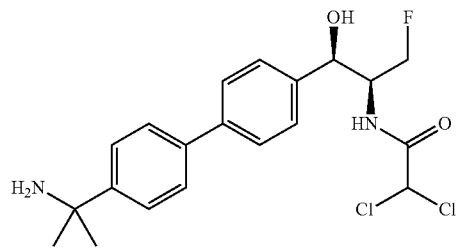 [SMILES: CC(C)(N)c1ccc(-c2ccc([C@@H](O)[C@@H](CF)NC(=O)C(Cl)Cl)cc2)cc1]

Step 1: Preparation of tert-butyl (2-(4'-((4S,5R)-3-(2,2-dichloroacetyl)-4-(fluoromethyl)-2,2-dimethyloxazolidin-5-yl)-[1,1'-biphenyl]-4-yl)propan-2-yl)carbamate

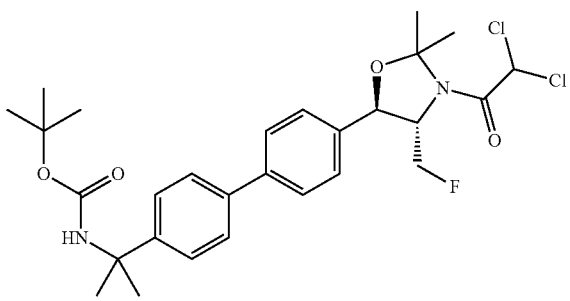 [SMILES: CC(C)(C)OC(=O)NC(C)(C)c1ccc(-c2ccc([C@H]3OC(C)(C)N(C(=O)C(Cl)Cl)[C@@H]3CF)cc2)cc1]

A mixture of tert-butyl (2-(4-(4,4,5,5-tetramethyl-1,3,2-dioxaborolan-2-yl)phenyl)-propan-2-yl)carbamate (previously described in Biorganic and Medicinal Chemistry Letters, 2007, 2179, 134 mg, 0.37 mmol), (4S,5R)-4-(fluoromethyl)-5-(4-iodophenyl)-2,2-dimethyloxazolidine (150 mg, 0.337 mmol), Cs$_2$CO$_3$ (240 mg, 0.72 mmol) in dioxane (4 mL) and water (1 mL) is bubbled with nitrogen gas for 2 minutes. To this mixture is added Pd(PPh$_3$)$_4$ (54 mg, 0.047 mmol) and the resulting reaction mixture heated at 80°

C. in microwave reactor for 4 hours. Reaction is diluted with water (10 ml) and extracted with ethyl acetate. Combined organic solution is dried over Na$_2$SO$_4$ and concentrated. Crude product is absorbed on celite, and purified on silica gel column using 0 to 30% EtOAC/heptane to give the title compound (120 mg). $^1$H NMR (400 MHz, CDCl$_3$) δ: (1H-NMR) 1.42 (bs, 9H), 1.67 (bs, 9H), 1.74 (bs, 3H) 4.47-4.74 (bm, 1.5H), 4.76-4.87 (bm 0.5H) 4.95-5.12 (bm, 1.5H) 5.16-5.31 (bm, 0.5H), 6.24-6.46 (bs, 1H), 7.47-7.53 (m, 4H), 7.56 (d, 2H, J=8.0 Hz), 7.64 (d, 2H, J=8.0 Hz).

Step 2: Preparation of N-((1R,2S)-1-(4'-(2-aminopropan-2-yl)-[1,1'-biphenyl]-4-yl)-3-fluoro-1-hydroxypropan-2-yl)-2,2-dichloroacetamide To a solution of the product of Step 1 (50 mg. 0.09 mmol) in DCM (1 mL) is added TFA (0.25 mL) and stirred at room temperature for 1 hour. Reaction is diluted with toluene (5 mL) and concentrated. Crude product is dissolved in DCM (0.5 mL) and DIPEA (200 µL), adsorbed on celite and purified on silica gel column eluting from 5 to 20% MeOH/DCM. The combined fractions are concentrated to give an oil, which is basified using saturated aqueous NaHCO$_3$ (0.5 mL), and extracted with ethyl acetate (3×2 mL). The combined extracts are dried over Na$_2$SO$_4$ and concentrated to give the title compound (3 mg). $^1$H NMR (400 MHz, CD$_3$OD) δ 1.52 (s, 6H), 4.2-4.29 (m, 1.5H), 4.32-4.38 (m, 0.5H) 4.4-4.51 m, 1.5H), 4.55-4.61 (m, 0.5H), 4.89 (d, 1H, J=4.0 Hz) 6.19 (s, 1H), 7.38 (d, 2H, J=8.0 Hz), 7.45-7.50 (m, 3H), 7.51-7.56 (m, 3H). m/z (Cl) 396 [M-OH].

Example 5

Preparation of N-((1R,2S)-1-(4'-((R)-1-aminoethyl)-[1,1'-biphenyl]-4-yl)-3-fluoro-1-hydroxypropan-2-yl)-2,2-dichloroacetamide

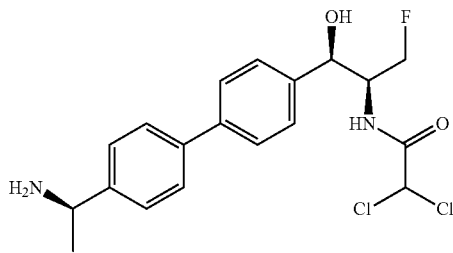 [SMILES: C[C@@H](N)c1ccc(-c2ccc([C@@H](O)[C@@H](CF)NC(=O)C(Cl)Cl)cc2)cc1]

Step 1: Preparation of tert-butyl ((R)-1-(4'-((4S,5R)-3-(2,2-dichloroacetyl)-4-(fluoromethyl)-2,2-dimethyloxazolidin-5-yl)-[1,1'-biphenyl]-4-yl)ethyl)carbamate

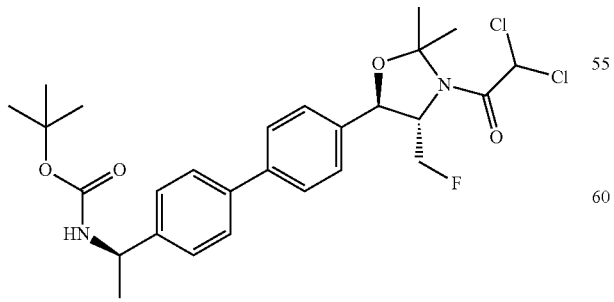

A mixture of commercially available (R)-tert-butyl (1-(4-(4,4,5,5-tetramethyl-1,3,2-dioxaborolan-2-yl)phenyl)ethyl)carbamate (194 mg, 0.559 mmol), the product of preparation 6 (250 mg, 0.56 mmol), Cs$_2$CO$_3$ (390 mg, 1.2 mmol) in dioxane (4 mL) and water (1 mL) is bubbled with nitrogen gas for 2 minutes. To this mixture Pd(PPh$_3$)$_4$ (90 mg, 0.078 mmol) is added and then resulting reaction mixture heated at 80° C. in microwave reactor for 4 hours. Reaction is diluted with water (10 ml) and extracted with ethyl acetate. Combined organic solution is dried over Na$_2$SO$_4$ and concentrated. Crude product is adsorbed on celite, and purified on silica gel column using 0 to 30% EtOAC/heptane to give the title compound (130 mg). $^1$H NMR (400 MHz, CDCl$_3$) δ 1.45 (bs, 9H), 1.50 (d, 3H, J=8.0 Hz) 1.68 (bs, 3H), 1.74 (bs, 3H) 4.49-4.74 (bm, 2H), 4.77-4.93 (bm 2H) 4.99-5.10 (bm, 1H) 6.28-6.44 (bs, 1H), 7.40 (d, 2H, J=8.0 Hz), 7.51 (d, 2H, J=8.0 Hz), 7.57 (d, 2H, J=8.0 Hz), 7.63 (d, 2H, J=8.0 Hz).

Step 2: Preparation of N-((1R,2S)-1-(4'-((R)-1-aminoethyl)-[1,1'-biphenyl]-4-yl)-3-fluoro-1-hydroxypropan-2-yl)-2,2-dichloroacetamide To a solution of the product of step 1 (130 mg. 0.241 mmol) in DCM (3 mL) is added TFA (0.7 mL) and stirred at room temperature for 1 hour. Reaction is diluted with toluene (10 mL) and concentrated. The crude product is dissolved in DMF (2 mL) and DIPEA (200 µL), and purified using HPLC eluting from 5% acetonitrile/water to 100 acetonitrile/water to give the title compound (60 mg). $^1$H NMR (400 MHz, CD$_3$OD) δ 1.69 (d, 3H, J=4.0 Hz), 4.31-4.41 (m, 1.5H), 4.44-4.55 (m, 1.5H) 4.56-4.63 (m, 0.5H), 4.68-4.74 (m, 0.5H), 5.02 (d, 1H, J=4.0 Hz) 6.31 (s, 1H), 7.48-7.57 (m, 4H), 7.63 (d, 2H, J=8.0 Hz), 7.72 (d, 2H, J=8.0 Hz). m/z (Cl) 382 [M-OH].

Example 6

Preparation of 2,2-dichloro-N-((1R,2S)-3-fluoro-1-hydroxy-1-(4'-(pyrrolidin-2-yl)-[1,1'-biphenyl]-4-yl)propan-2-yl)acetamide

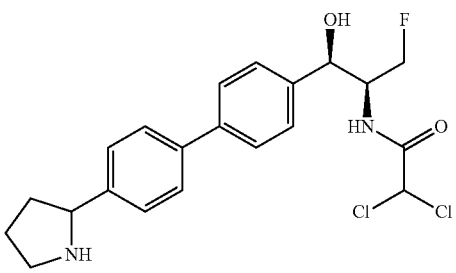 [SMILES: O=C(N[C@H](CF)[C@H](O)c1ccc(-c2ccc(C3CCCN3)cc2)cc1)C(Cl)Cl]

Step 1: Preparation of tert-butyl 2-(4'-((1R,2S)-2-(2,2-dichloroacetamido)-3-fluoro-1-hydroxypropyl)-[1,1'-biphenyl]-4-yl)pyrrolidine-1-carboxylate

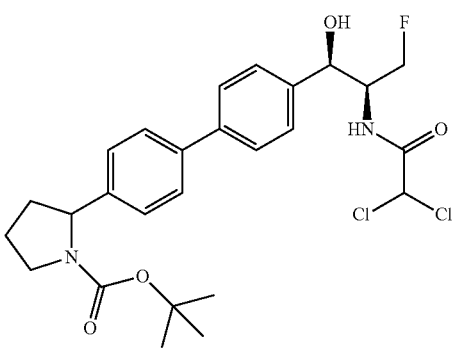 [SMILES: CC(C)(C)OC(=O)N1CCCC1c1ccc(-c2ccc([C@@H](O)[C@@H](CF)NC(=O)C(Cl)Cl)cc2)cc1]

A mixture of commercially available 2-(4-Bromo-phenyl)-pyrrolidine-1-carboxylic acid tert-butyl ester (500 mg, 1.53 mmol), 2,2-dichloro-N-((1R,2S)-3-fluoro-1-hydroxy-1-(4-(trimethylstannyl)phenyl)propan-2-yl)acetamide (679 mg, 1.53 mmol, 1 eq.), P(2-fur)3 (72 mg, 0.31 mmol, 0.2 eq.) and Pd₂(dba)₃ (142 mg, 0.153 mmol, 0.1 eq.) are dissolved in DMF (8 mL, 0.2 M) and de-oxygenated. The mixture is heated to 80° C. for 16 hours. Reaction is concentrated under vacuum to a syrup and purified on a 24 g silica column eluting from 0-100% EtOAc/heptane) to give the title compound 240 mg.
¹HNMR (400 MHz, CD₃Cl) δ 1.2-1.6 (9H), 1.8-2.0 (3H), 2.3-2.4 (1H), 2.5 (1H), 3.6-3.7 (2H), 4.25-4.4 (1H), 4.4-4.5 (0.5H), 4.5-4.65 (1H), 4.65-4.8 (0.5H), 4.8-4.9 (0.5H), 5.0-5.1 (0.5H), 5.1-5.2 (1H), 5.9 (1H), 7.0-7.1 (2H), 7.4-7.65 (7H).

Step 2: Preparation of 2,2-dichloro-N-((1R,2S)-3-fluoro-1-hydroxy-1-(4'-(pyrrolidin-2-yl)-[1,1'-biphenyl]-4-yl)propan-2-yl)acetamide To a solution of the product of step 1 (210 mg, 0.4 mmol) in DCM (3 mL) is added TFA (1 mL). The mixture is stirred for 1 hour. The reaction is then diluted with DCM, washed with sat.NaHCO₃ (aq.) and evaporated to give the title compound (144 mg). ¹H-NMR (400 MHz, DMSO) δ(ppm) 1.5-1.65 (1H), 1.7-1.9 (2H), 2.1-2.25 (1H), 2.8-3.0 (1H), 3.0-3.2 (1H), 4.05-4.15 (1H), 4.15-4.35 (1.5H), 4.35-4.45 (0.5H), 4.5-4.6 (0.5H), 4.65-4.75 (0.5H), 4.8-4.9 (1H), 5.9-6.0 (1H), 6.5 (1H), 7.4-7.5 (4H), 7.5-7.65 (4H), 8.6 (1H).

Example 7

Preparation of N-((1R,2S)-1-(4'-(azetidin-2-yl)-[1,1'-biphenyl]-4-yl)-3-fluoro-1-hydroxypropan-2-yl)-2,2-dichloroacetamide

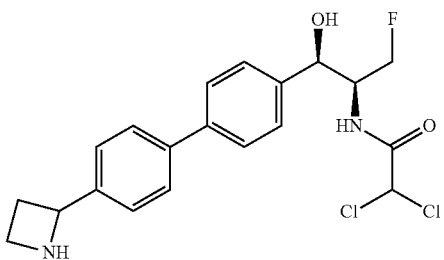 [SMILES: O=C(N[C@H](CF)[C@H](O)c1ccc(-c2ccc(C3CCN3)cc2)cc1)C(Cl)Cl]

Step 1: Preparation of tert-butyl 2-(4'-((1R,2S)-2-(2,2-dichloroacetamido)-3-fluoro-1-hydroxypropyl)-[1,1'-biphenyl]-4-yl)azetidine-1-carboxylate

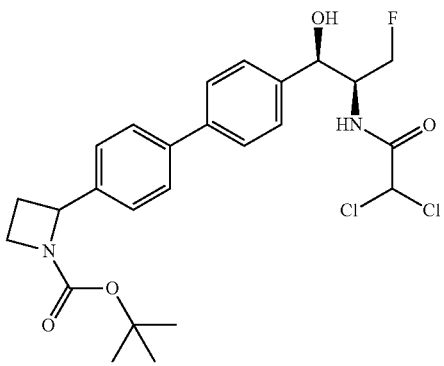 [SMILES: CC(C)(C)OC(=O)N1CCC1c1ccc(-c2ccc([C@@H](O)[C@@H](CF)NC(=O)C(Cl)Cl)cc2)cc1]

Following the general procedure of Example 6, step 1, and making non-critical variations but using tert-butyl 2-(4-bromophenyl)azetidine-1-carboxylate, the title compound is obtained: ¹HNMR (400 MHz, CD₃Cl) δ(ppm) 1.25-1.5 (9H), 2.1-2.25 (1H), 2.6-2.75 (1H), 3.3 (1H), 4-4.1 (t, 2H), 4.3-4.4 (1.5H), 4.4-4.5 (0.5H), 4.5-4.6 (1.5H), 4.65-4.75 (0.5H), 5.05-5.15 (1H), 5.2-5.3 (1H), 5.9-6.0 (1H), 7.1-7.2 (2H), 7.4-7.5 (4H), 7.55-7.65 (4H).

Step 2: Preparation of N-((1R,2S)-1-(4'-(azetidin-2-yl)-[1,1'-biphenyl]-4-yl)-3-fluoro-1-hydroxypropan-2-yl)-2,2-dichloroacetamide

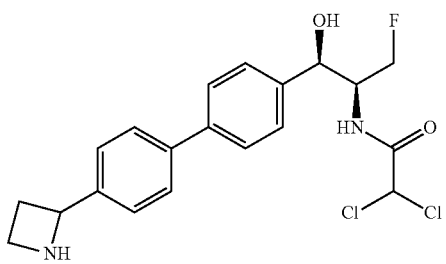 [SMILES: O=C(N[C@H](CF)[C@H](O)c1ccc(-c2ccc(C3CCN3)cc2)cc1)C(Cl)Cl]

Following the general procedure of Example 6, step 2, and making non-critical variations but using the product of step 1 of Example 6, the title compound is obtained. ¹HNMR (400 MHz, DMSO) δ(ppm) 1.9-2.05 (1H), 2.05-2.2 (1H), 3.05-3.2 (1H), 4.05-4.4 (1.5H), 4.4-4.5 (0.5H), 4.5-4.6 (0.5H), 4.6-4.7 (0.5H), 4.9-5.0 (1H), 5.4-5.5 (1H), 5.9-6.0 (1H), 6.5 (1H), 7.4 (1H), 7.4-7.5 (4H), 7.55-7.65 (4H), 8.6 (1H). m/z (CI) M+H 410.

Example 8

2,2-dichloro-N-((1R,2S)-3-fluoro-1-(4'-((3-fluoroazetidin-1-yl)methyl)-[1,1'-biphenyl]-4-yl)-1-hydroxypropan-2-yl)acetamide

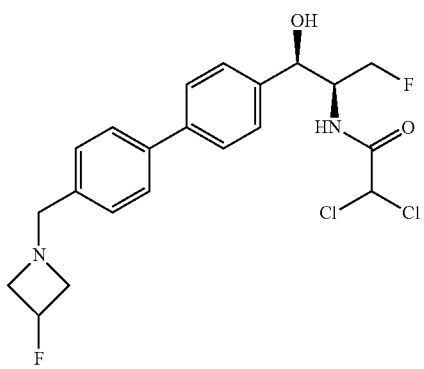 [SMILES: O=C(N[C@H](CF)[C@H](O)c1ccc(-c2ccc(CN3CC(F)C3)cc2)cc1)C(Cl)Cl]

Step 1: Preparation of 2,2-dichloro-1-((4S,5R)-5-(4'-((3-fluoroazetidin-1-yl)methyl)-[1,1'-biphenyl]-4-yl)-4-(fluoromethyl)-2,2-dimethyloxazolidin-3-yl)ethanone

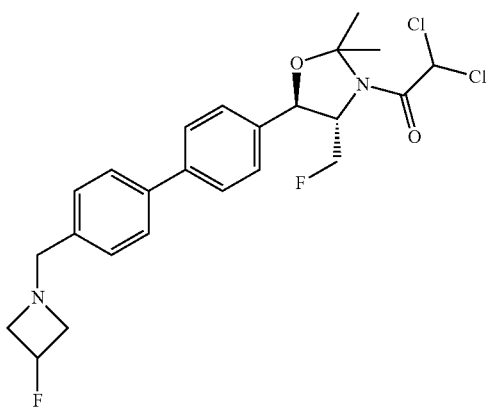 [SMILES: CC1(C)O[C@H](c2ccc(-c3ccc(CN4CC(F)C4)cc3)cc2)[C@@H](CF)N1C(=O)C(Cl)Cl]

To a mixture of the product of preparation 8 (1.0 g, 2.24 mmol) and commercially available hydroxylamine hydrochloride (313 mg, 2.81 mmol) in DMF (10 mL) is added DIEA (0.800 mL, 4.5 mmol) and the mixture stirred at 60° C. for 2 hours. Reaction is diluted with water (50 mL) and extracted using ethyl acetate (3×50 mL). Organic solution is washed with water, dried over $Na_2SO_4$, and concentrated to give a syrup. Crude compound adsorbed on celite and purified on silica gel column eluting from 20 to 60% EtOAcheptane to give the title compound (880 mg): $^1$HNMR (400 MHz, DMSO-$d_6$) δ: (1H-NMR) 1.50 (s, 3H), 1.61 (s, 3H), 3.08-3.21 (m, 2H), 3.49-3.62 (m, 2H), 3.66 (s, 2H), 4.47-4.57 (m, 0.5H), 4.60-4.76 (m, 1H), 4.80-4.97 (m, 1.5H), 5.07-5.17 (m, 0.5H), 5.19-5.29 (m, 1.5H), 7.03 (s, 1H), 7.36 (d, 1H, J=8 Hz), 7.54 (d, 1H, J=8.0 Hz), 7.64 (d, 1H, J=8.0 Hz), 7.71 (d, 1H, J=8.0 Hz), (m/z (Cl) 383 [M$^+$].

Step 2: Preparation of 2,2-dichloro-N-((1R,2S)-3-fluoro-1-(4'-((3-fluoroazetidin-1-yl)methyl)[1,1'-biphenyl]-4-yl)-1-hydroxypropan-2-yl)acetamide

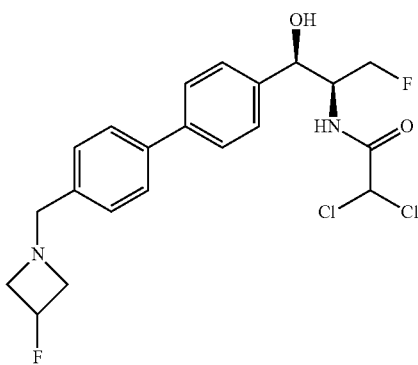 [SMILES: O=C(N[C@H](CF)[C@H](O)c1ccc(-c2ccc(CN3CC(F)C3)cc2)cc1)C(Cl)Cl]

To a slurry of the product of step 1 (875 mg, 1.81 mmol) in water (10 mL) is added 4 N HCl in dioxane (7 mL) and the mixture stirred at room temperature for 24 hours. Reaction is cooled with ice water and basified slowly using solid $NaHCO_3$. The mixture is partitioned between ethylacetate and brine and subsequently extracted with ethyl acetate (3×30 mL). Combined extracts are dried over $Na_2SO_4$ and concentrated. Crude product dissolved in ethyl acetate (2 mL), adsorbed on celite and purified on silica gel eluting from 40 to 80% ethyl acetateheptane to give the title compound (560 mg). $^1$HNMR (400 MHz, DMSO-$d_6$) δ: (1H-NMR) 3.07-3.20 (m, 2H), 3.49-3.61 (m, 2H), 3.66 (s, 2H), 4.14-4.32 (m, 1.5H), 4.36-4.44 (m, 0.5H), 4.54-4.60 (m, 0.5H), 4.65-4.72 (m, 0.5H), 4.85-4.91 (m, 1H), 5.07-5.14 (m, 0.5H), 5.21-5.29 (m, 0.5H), 5.95 (d, 1H, J=4.0 Hz), 6.53 (s, 1H), 7.34 (d, 1H, J=8 Hz), 7.42 (d, 1H, J=8.0 Hz), 7.57-7.63 (m, 4H), 8.61 (d, 1H, J=8 Hz), (m/z (Cl) 443 [M$^+$+1].

Following Example 8 and making non-critical variations, the compounds of Examples 9-19 are made.

Example 9

2,2-dichloro-N-((1R,2S)-3-fluoro-1-(4'-((3-fluoroazetidin-1-yl)methyl)-[1,1'-biphenyl]-4-yl)-1-hydroxypropan-2-yl)acetamide

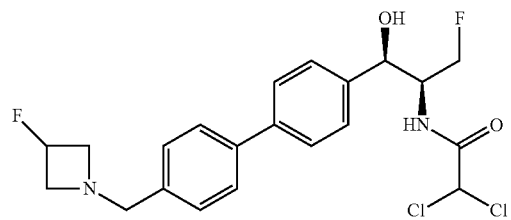 [SMILES: O=C(N[C@H](CF)[C@H](O)c1ccc(-c2ccc(CN3CC(F)C3)cc2)cc1)C(Cl)Cl]

Example 10

2,2-dichloro-N-((1R,2S)-3-fluoro-1-hydroxy-1-(4'-((3-((methylamino)methyl)-azetidin-1-yl)methyl)-[1,1'-biphenyl]-4-yl)propan-2-yl)acetamide

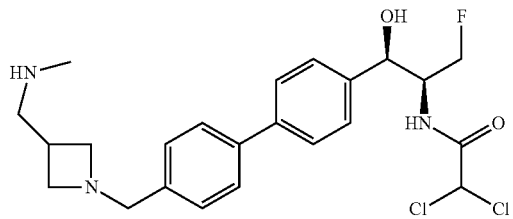 [SMILES: CNCC1CN(Cc2ccc(-c3ccc([C@@H](O)[C@@H](CF)NC(=O)C(Cl)Cl)cc3)cc2)C1]

Example 11

2,2-dichloro-N-((1R,2S)-3-fluoro-1-hydroxy-1-(4'-((3-hydroxyazetidin-1-yl)methyl)-[1,1'-biphenyl]-4-yl)propan-2-yl)acetamide

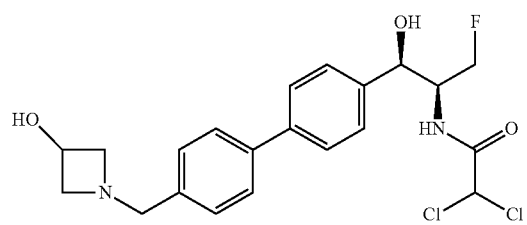 [SMILES: O=C(N[C@H](CF)[C@H](O)c1ccc(-c2ccc(CN3CC(O)C3)cc2)cc1)C(Cl)Cl]

Example 12

2,2-dichloro-N-((1R,2S)-1-(4'-((3-(dimethylamino)azetidin-1-yl)methyl)-[1,1'-biphenyl]-4-yl)-3-fluoro-1-hydroxypropan-2-yl)acetamide

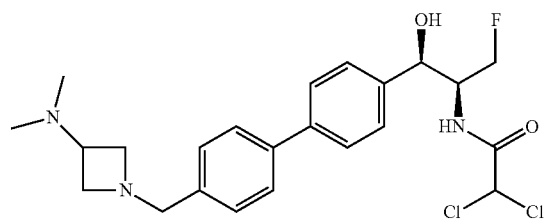 [SMILES: CN(C)C1CN(Cc2ccc(-c3ccc([C@@H](O)[C@@H](CF)NC(=O)C(Cl)Cl)cc3)cc2)C1]

Example 13

N-((1R,2S)-1-(4'-((3-(aminomethyl)azetidin-1-yl)methyl)-[1,1'-biphenyl]-4-yl)-3-fluoro-1-hydroxypropan-2-yl)-2,2-dichloroacetamide

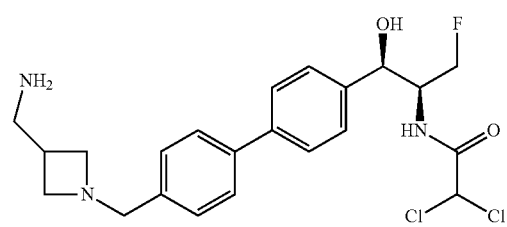 [SMILES: NCC1CN(Cc2ccc(-c3ccc([C@@H](O)[C@@H](CF)NC(=O)C(Cl)Cl)cc3)cc2)C1]

Example 14

2,2-dichloro-N-((1R,2S)-3-fluoro-1-hydroxy-1-(4'-((3-methoxyazetidin-1-yl)methyl)-[1,1'-biphenyl]-4-yl)propan-2-yl)acetamide

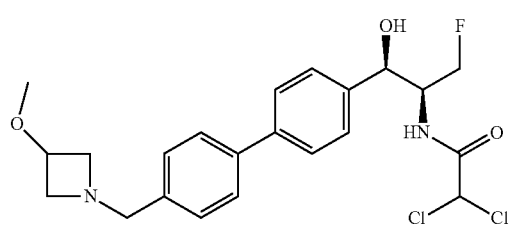 [SMILES: COC1CN(Cc2ccc(-c3ccc([C@@H](O)[C@@H](CF)NC(=O)C(Cl)Cl)cc3)cc2)C1]

Example 15

N-((1R,2S)-1-(4'-((3-acetamidoazetidin-1-yl)methyl)-[1,1'-biphenyl]-4-yl)-3-fluoro-1-hydroxypropan-2-yl)-2,2-dichloroacetamide

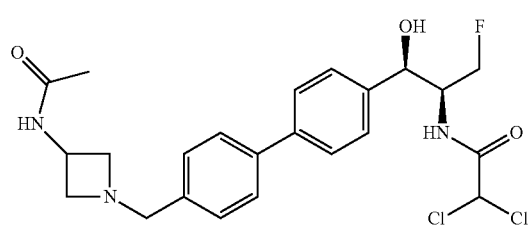 [SMILES: CC(=O)NC1CN(Cc2ccc(-c3ccc([C@@H](O)[C@@H](CF)NC(=O)C(Cl)Cl)cc3)cc2)C1]

Example 16

N-((1R,2S)-1-(4'-((3-aminoazetidin-1-yl)methyl)-[1,1'-biphenyl]-4-yl)-3-fluoro-1-hydroxypropan-2-yl)-2,2-dichloroacetamide

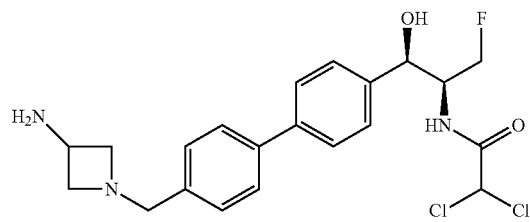 [SMILES: NC1CN(Cc2ccc(-c3ccc([C@@H](O)[C@@H](CF)NC(=O)C(Cl)Cl)cc3)cc2)C1]

Example 17

2,2-dichloro-N-((1R,2S)-3-fluoro-1-hydroxy-1-(4'-((3-hydroxy-3-(trifluoromethyl)azetidin-1-yl)methyl)-[1,1'-biphenyl]-4-yl)propan-2-yl)acetamide

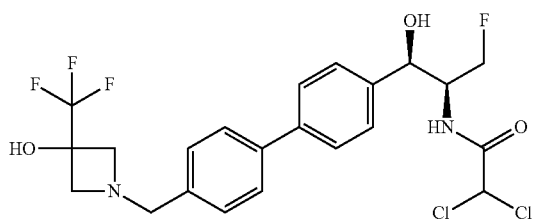 [SMILES: O=C(N[C@H](CF)[C@H](O)c1ccc(-c2ccc(CN3CC(O)(C(F)(F)F)C3)cc2)cc1)C(Cl)Cl]

Example 18

2,2-dichloro-N-((1R,2S)-3-fluoro-1-hydroxy-1-(4'-((3-(trifluoromethyl)azetidin-1-yl)methyl)-[1,1'-biphenyl]-4-yl)propan-2-yl)acetamide

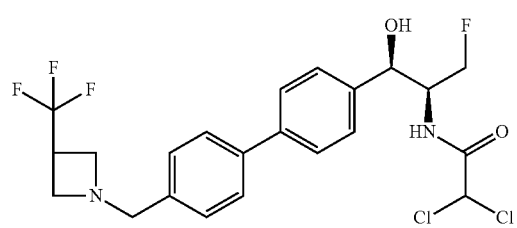 [SMILES: O=C(N[C@H](CF)[C@H](O)c1ccc(-c2ccc(CN3CC(C(F)(F)F)C3)cc2)cc1)C(Cl)Cl]

Example 19

N-((1R,2S)-1-(4'-((3-(aminomethyl)-3-hydroxyazetidin-1-yl)methyl)-[1,1'-biphenyl]-4-yl)-3-fluoro-1-hydroxypropan-2-yl)-2,2-dichloroacetamide

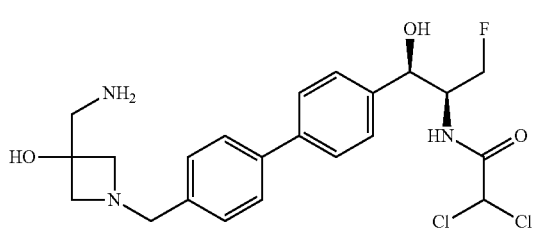 [SMILES: NCC1(O)CN(Cc2ccc(-c3ccc([C@@H](O)[C@@H](CF)NC(=O)C(Cl)Cl)cc3)cc2)C1]

Example 20

2,2-dichloro-N-((1R,2S)-3-fluoro-1-hydroxy-1-(4'-((R)-1-(methylsulfonamido)-ethyl)biphenyl-4-yl)propan-2-yl)acetamide

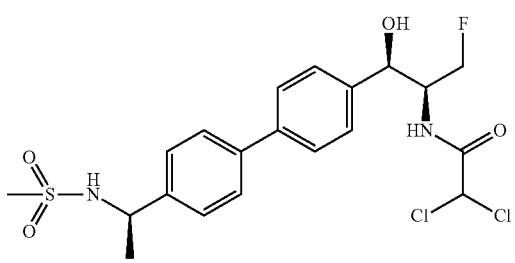 [SMILES: C[C@@H](NS(C)(=O)=O)c1ccc(-c2ccc([C@@H](O)[C@@H](CF)NC(=O)C(Cl)Cl)cc2)cc1]

To a solution of product of Example 5 (120 mg, 0.30 mmol) in DCM (3 mL) is added di-isopropylethylamine (0.026 mL, 0.33 mmol) and then methanesulfonyl chloride (0.080 mL, 0.45 mmol). The mixture is stirred at room temperature for 1 hour, concentrated and adsorbed on silica and chromatographed on silica eluting with 40-100% ethyl acetate in heptane to give compound X (105 mg). 1H-NMR (400 MHz, CDCl3) δ: 1.60 (d, 3H, J=6 Hz), 2.72 (s, 3H), 4.3-4.8 (m, 5H), 5.20 (m, 1H), 5.90 (s, 1H), 7.08 (d, 1H, J=6 Hz), 7.4-7.6 (m, 4H), 7.6-7.7 (m, 4H). m/z (Cl) 501 (M+Na)

Example 21

N-((1R,2S)-1-(4'-(1-aminocyclopropyl)-[1,1'-biphenyl]-4-yl)-3-fluoro-1-hydroxypropan-2-yl)-2,2-dichloroacetamide

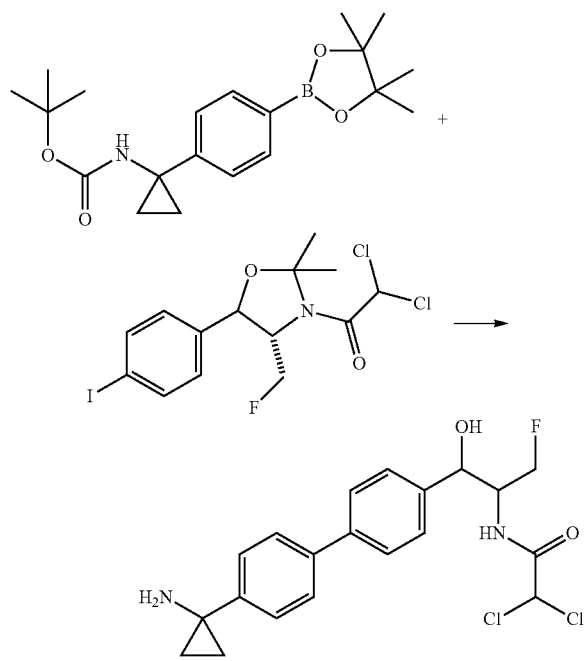

A mixture of tert-butyl (1-(4-(4,4,5,5-tetramethyl-1,3,2-dioxaborolan-2-yl)phenyl)cyclopropyl)carbamate (252 mg, 0.7 mmol), 2,2-dichloro-1-((4S,5R)-4-(fluoromethyl)-5-(4-iodophenyl)-2,2-dimethyloxazolidin-3-yl)ethanone (250 mg, 0.56 mmol), Cs₂CO₃ (365 mg, 1.12 mmol) in dioxane (4 mL) and water (1 mL) is bubbled with nitrogen gas for 2 minutes. Pd(PPh₃)₄ (64 mg, 0.056 mmol) is added and the resulting reaction mixture heated at 80° C. for 4 hours. After cooling to room temperature, the reaction is diluted with water (10 ml) and extracted with ethyl acetate (3×10 mL). Combined organic extracts are dried over Na₂SO₄ and concentrated. Crude compound dissolved in DCM (3 mL) and stirred with TFA (0.6 mL) at room temperature for 1 hour. Reaction is diluted with toluene (10 mL) and concentrated to a syrup. Crude compound is basified slowly using saturated aq. NaHCO₃, saturated with NaCl, and extracted with ethyl acetate (3×30 mL). Combined extracts dried over Na₂SO₄ and concentrated. Solid dissolved in DMF (2 mL) and purified using HPLC eluting from 5 to 95% water/acetonitrile to give the title compound (90 mg): 1HNMR (400 MHz, DMSO-d₆) δ: 1.16-1.28 (m, 2H), 1.31-1.41 (m, 2H), 4.15-4.36 (m, 1.5H), 4.38-4.47 (m, 0.5H) 4.55-4.62 (m, 0.5H), 4.65-4.74 (m, 0.5H), 4.90 (bs, 1H) 5.98 (bs, 1H), 6.54 (bs, 1H), 7.41-7.53 (m, 4H), 7.64 (d, 2H, J=8.0 Hz), 7.72 (d, 2H, J=8.0 Hz), 8.63 (d, 1H, J=8 Hz), 8.66-8.79 (bs, 3H), m/z (Cl) 411 [M+1].

Example 22

N-((1R,2S)-1-(3'-(1-aminocyclopropyl)-[1,1'-biphenyl]-4-yl)-3-fluoro-1-hydroxypropan-2-yl)-2,2-dichloroacetamide

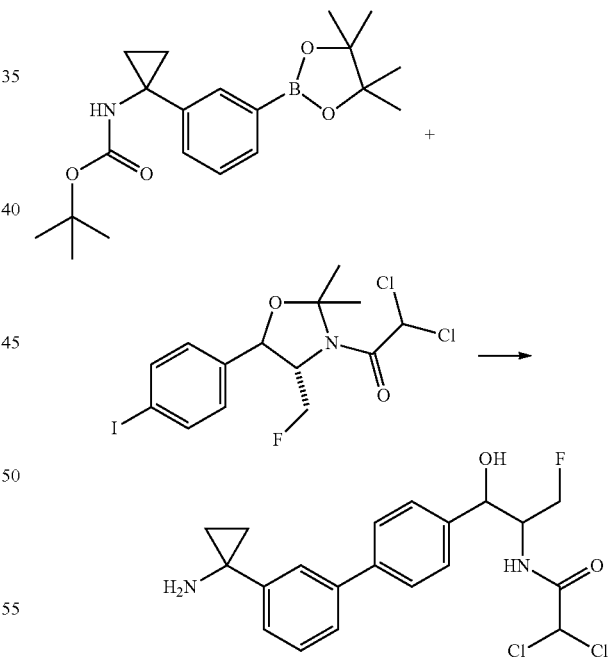

A mixture of tert-butyl (1-(3-(4,4,5,5-tetramethyl-1,3,2-dioxaborolan-2-yl)phenyl)cyclopropyl)carbamate (241 mg, 0.672 mmol), 2,2-dichloro-1-((4S,5R)-4-(fluoromethyl)-5-(4-iodophenyl)-2,2-dimethyloxazolidin-3-yl)ethanone (250 mg, 0.56 mmol), Cs₂CO₃ (365 mg, 1.12 mmol) in dioxane (4 mL) and water (1 mL) is bubbled with nitrogen gas for 2 minutes. Pd(PPh₃)₄ (64 mg, 0.056 mmol) is added and the resulting reaction mixture heated at 80° C. for 4 hours. Reaction is diluted with water (10 ml) and extracted with ethyl acetate (3×10 mL). Combined organic solution is dried over Na₂SO₄ and concentrated. Crude compound dissolved in DCM (3 mL) and stirred with TFA (0.6 mL) at room temperature for 1 hour. Reaction is diluted with toluene (10 mL) and concentrated. Crude compound is basified slowly using saturated aq. NaHCO₃, extracted with ethyl acetate (3×30 mL) and combined extracts dried over Na₂SO₄ and concentrated. Solid dissolved in DMF (2 mL) and purified using HPLC eluting from 5 to 95% water/acetonitrile to give the title compound (50 mg): 1 HNMR (400 MHz, MeOH-d₄) δ: 1.33-1.39 (m, 2H), 1.40-1.47 (m, 2H), 4.33-4.42 (m, 1.5H), 4.44-4.51 (m, 0.5H) 4.56-4.63 (m, 0.5H), 4.68-4.75 (m, 0.5H), 5.03 (d, 1H, J=4 Hz), 6.31 (s, 1H), 7.44-7.48 (m, 1H), 7.50-5.55 9 m, 3H), 7.63-7.68 (m, 3H), 7.75-7.78 (m, 1H), m/z (Cl) 411 [M+1].

We claim:

1. A compound, which is:
   b) 2,2-Dichloro-N-((1R,2S)-3-fluoro-1-hydroxy-1-(4'-((3-methylureido)methyl)-[1,1'-biphenyl]-4-yl)propan-2-yl)acetamide,
   c) N-((1R,2S)-1-(4'-(2-aminopropan-2-yl)-[1,1'-biphenyl]-4-yl)-3-fluoro-1-hydroxypropan-2-yl)-2,2-dichloroacetamide,
   d) N-((1R,2S)-1-(4'-((R)-1-aminoethyl)-[1,1'-biphenyl]-4-yl)-3-fluoro-1-hydroxypropan-2-yl)-2,2-dichloroacetamide,
   e) 2,2-dichloro-N-((1R,2S)-3-fluoro-1-hydroxy-1-(4'-(pyrrolidin-2-yl)-[1,1'-biphenyl]-4-yl)propan-2-yl)acetamide,
   f) N-((1R,2S)-1-(4'-(azetidin-2-yl)-[1,1'-biphenyl]-4-yl)-3-fluoro-1-hydroxypropan-2-yl)-2,2-dichloroacetamide,
   g) 2,2-dichloro-N-((1R,2S)-3-fluoro-1-(4'-((3-fluoroazetidin-1-yl)methyl)-[1,1'-biphenyl]-4-yl)-1-hydroxypropan-2-yl)acetamide,
   h) 2,2-dichloro-N-((1R,2S)-3-fluoro-1-hydroxy-1-(4'-((3-((methylamino)methyl)azetidin-1-yl)methyl)-[1,1'-biphenyl]-4-yl)propan-2-yl)acetamide,
   i) 2,2-dichloro-N-((1R,2S)-3-fluoro-1-hydroxy-1-(4'-((3-hydroxyazetidin-1-yl)methyl)-[1,1'-biphenyl]-4-yl)propan-2-yl)acetamide,
   j) 2,2-dichloro-N-((1R,2S)-1-(4'-((3-(dimethylamino)azetidin-1-yl)methyl)-[1,1'-biphenyl]-4-yl)-3-fluoro-1-hydroxypropan-2-yl)acetamide,
   k) N-((1R,2S)-1-(4'-((3-(aminomethyl)azetidin-1-yl)methyl)-[1,1'-biphenyl]-4-yl)-3-fluoro-1-hydroxypropan-2-yl)-2,2-dichloroacetamide,
   l) 2,2-dichloro-N-((1R,2S)-3-fluoro-1-hydroxy-1-(4'-((3-methoxyazetidin-1-yl)methyl)-[1,1'-biphenyl]-4-yl)propan-2-yl)acetamide,
   m) N-((1R,2S)-1-(4'-((3-acetamidoazetidin-1-yl)methyl)-[1,1'-biphenyl]-4-yl)-3-fluoro-1-hydroxypropan-2-yl)-2,2-dichloroacetamide,
   n) N-((1R,2S)-1-(4'-((3-aminoazetidin-1-yl)methyl)-[1,1'-biphenyl]-4-yl)-3-fluoro-1-hydroxypropan-2-yl)-2,2-dichloroacetamide,
   o) 2,2-dichloro-N-((1R,2S)-3-fluoro-1-hydroxy-1-(4'-((3-hydroxy-3-(trifluoromethyl)azetidin-1-yl)methyl)-[1,1'-biphenyl]-4-yl)propan-2-yl)acetamide,
   p) 2,2-dichloro-N-((1R,2S)-3-fluoro-1-hydroxy-1-(4'-((3-(trifluoromethyl)azetidin-1-yl)methyl)-[1,1'-biphenyl]-4-yl)propan-2-yl)acetamide,
   q) N-((1R,2S)-1-(4'-((3-(aminomethyl)-3-hydroxyazetidin-1-yl)methyl)-[1,1'-biphenyl]-4-yl)-3-fluoro-1-hydroxypropan-2-yl)-2,2-dichloroacetamide,
   r) 2,2-dichloro-N-((1R,2S)-3-fluoro-1-hydroxy-1-(4'-((R)-1-(methylsulfonamido)-ethyl)biphenyl-4-yl)propan-2-yl)acetamide,
   s) N-((1R,2S)-1-(4'-(1-aminocyclopropyl)-[1,1'-biphenyl]-4-yl)-3-fluoro-1-hydroxypropan-2-yl)-2,2-dichloroacetamide, or
   t) N-((1R,2S)-1-(3'-(1-aminocyclopropyl)-[1,1'-biphenyl]-4-yl)-3-fluoro-1-hydroxypropan-2-yl)-2,2-dichloroacetamide.

2. A compound, which is:
   a) 2,2-Dichloro-N-((1R,2S)-3-fluoro-1-hydroxy-1-(4'-((3-methylureido)methyl)-[1,1'-biphenyl]-4-yl)propan-2-yl)acetamide,
   b) N-((1R,2S)-1-(4'-(2-aminopropan-2-yl)-[1,1'-biphenyl]-4-yl)-3-fluoro-1-hydroxypropan-2-yl)-2,2-dichloroacetamide,
   c) N-((1R,2S)-1-(4'-((R)-1-aminoethyl)-[1,1'-biphenyl]-4-yl)-3-fluoro-1-hydroxypropan-2-yl)-2,2-dichloroacetamide,
   d) 2,2-dichloro-N-((1R,2S)-3-fluoro-1-hydroxy-1-(4'-(pyrrolidin-2-yl)-[1,1'-biphenyl]-4-yl)propan-2-yl)acetamide,
   e) N-((1R,2S)-1-(4'-(azetidin-2-yl)-[1,1'-biphenyl]-4-yl)-3-fluoro-1-hydroxypropan-2-yl)-2,2-dichloroacetamide,
   f) 2,2-dichloro-N-((1R,2S)-3-fluoro-1-(4'-((3-fluoroazetidin-1-yl)methyl)-[1,1'-biphenyl]-4-yl)-1-hydroxypropan-2-yl)acetamide,
   g) 2,2-dichloro-N-((1R,2S)-3-fluoro-1-hydroxy-1-(4'-((3-((methylamino)methyl)azetidin-1-yl)methyl)-[1,1'-biphenyl]-4-yl)propan-2-yl)acetamide,
   h) 2,2-dichloro-N-((1R,2S)-3-fluoro-1-hydroxy-1-(4'-((3-hydroxyazetidin-1-yl)methyl)-[1,1'-biphenyl]-4-yl)propan-2-yl)acetamide,
   i) 2,2-dichloro-N-((1R,2S)-1-(4'-((3-(dimethylamino)azetidin-1-yl)methyl)-[1,1'-biphenyl]-4-yl)-3-fluoro-1-hydroxypropan-2-yl)acetamide,
   j) N-((1R,2S)-1-(4'-((3-(aminomethyl)azetidin-1-yl)methyl)-[1,1'-biphenyl]-4-yl)-3-fluoro-1-hydroxypropan-2-yl)-2,2-dichloroacetamide,
   k) 2,2-dichloro-N-((1R,2S)-3-fluoro-1-hydroxy-1-(4'-((3-methoxyazetidin-1-yl)methyl)-[1,1'-biphenyl]-4-yl)propan-2-yl)acetamide,
   l) N-((1R,2S)-1-(4'-((3-acetamidoazetidin-1-yl)methyl)-[1,1'-biphenyl]-4-yl)-3-fluoro-1-hydroxypropan-2-yl)-2,2-dichloroacetamide,
   m) N-((1R,2S)-1-(4'-((3-aminoazetidin-1-yl)methyl)-[1,1'-biphenyl]-4-yl)-3-fluoro-1-hydroxypropan-2-yl)-2,2-dichloroacetamide,
   n) 2,2-dichloro-N-((1R,2S)-3-fluoro-1-hydroxy-1-(4'-((3-hydroxy-3-(trifluoromethyl)azetidin-1-yl)methyl)-[1,1'-biphenyl]-4-yl)propan-2-yl)acetamide,
   o) 2,2-dichloro-N-((1R,2S)-3-fluoro-1-hydroxy-1-(4'-((3-(trifluoromethyl)azetidin-1-yl)methyl)-[1,1'-biphenyl]-4-yl)propan-2-yl)acetamide,
   p) N-((1R,2S)-1-(4'-((3-(aminomethyl)-3-hydroxyazetidin-1-yl)methyl)-[1,1'-biphenyl]-4-yl)-3-fluoro-1-hydroxypropan-2-yl)-2,2-dichloroacetamide,
   q) N-((1R,2S)-1-(4'-(1-aminocyclopropyl)-[1,1'-biphenyl]-4-yl)-3-fluoro-1-hydroxypropan-2-yl)-2,2-dichloroacetamide, or
   r) N-((1R,2S)-1-(3'-(1-aminocyclopropyl)-[1,1'-biphenyl]-4-yl)-3-fluoro-1-hydroxypropan-2-yl)-2,2-dichloroacetamide.

* * * * *